United States Patent [19]
Hashiguchi et al.

[11] Patent Number: 5,863,518
[45] Date of Patent: Jan. 26, 1999

[54] DIAGNOSTIC IMAGING AGENT WITH BACKBONE WITH MODIFIED SUGAR CHAIN END

[75] Inventors: Yuji Hashiguchi; Hideki Sugino; Kenji Kamimura, all of Sodegaura; Shigemi Seri, Ichihara, all of Japan

[73] Assignee: Nihon Medi-Physics Co., Ltd., Hyogo, Japan

[21] Appl. No.: 544,548

[22] Filed: Oct. 18, 1995

[30] Foreign Application Priority Data

Oct. 21, 1994 [JP] Japan ................................. 6-282800

[51] Int. Cl.⁶ .......................... A61K 51/00; A61M 36/14
[52] U.S. Cl. ........................ 424/1.73; 424/1.65; 424/1.11
[58] Field of Search ................. 424/1.65, 1.73, 424/9.35, 9.42, 1.11; 534/10, 14, 15

[56] References Cited

U.S. PATENT DOCUMENTS

| | | | |
|---|---|---|---|
| 4,666,697 | 5/1987 | Takahashi et al. | 530/300 |
| 4,822,594 | 4/1989 | Gibby | 424/9.35 |
| 4,985,233 | 1/1991 | Klaveness et al. | 424/9.35 |
| 5,077,389 | 12/1991 | Takahashi et al. | 530/382 |
| 5,155,215 | 10/1992 | Ranney | 534/16 |
| 5,250,672 | 10/1993 | Sodler et al. | 424/9.33 |
| 5,271,924 | 12/1993 | Hashiguchi et al. | 424/9.35 |
| 5,271,929 | 12/1993 | Hashiguchi et al. | 424/9.35 |
| 5,312,908 | 5/1994 | Nakao | 536/20 |
| 5,330,743 | 7/1994 | Gibby et al. | 424/9 |
| 5,352,431 | 10/1994 | Hashiguchi et al. | 424/9.42 |
| 5,384,401 | 1/1995 | Takahashi et al. | 536/18.7 |
| 5,422,095 | 6/1995 | Hashiguchi et al. | 424/1.74 |

FOREIGN PATENT DOCUMENTS

| | | |
|---|---|---|
| A3551193 | 9/1993 | Australia . |
| B3551193 | 9/1993 | Australia . |
| 2139374 | 7/1995 | Canada . |
| 111311 | 6/1984 | European Pat. Off. . |
| 184899 | 6/1986 | European Pat. Off. . |
| 186947 | 7/1986 | European Pat. Off. . |
| 326226 | 8/1989 | European Pat. Off. . |
| 523572 | 1/1993 | European Pat. Off. . |
| 535668 | 4/1993 | European Pat. Off. . |
| 563013 | 9/1993 | European Pat. Off. . |
| 661279 | 7/1995 | European Pat. Off. . |
| 64/54028 | 3/1989 | Japan . |
| 1-100187 | 4/1989 | Japan . |
| 3C177426 | 6/1995 | Norway . |
| WO 85 05554 | 12/1985 | WIPO . |
| WO 87 01594 | 3/1987 | WIPO . |
| WO 87 02893 | 5/1987 | WIPO . |

OTHER PUBLICATIONS

Yoshikawa, K., et al., Journal of Medical Imagings 6, 959–969 (1986) (Summary at p. 969 in English).

Ogan, M. D., et al, Investigative Radiology, 22, 665–671 (Aug./1987).

Wang, Shih–Chang, et al, Radiology, 175: 483–488 (1990).

Sieving, P., et al, Society of Magnetic Resonance in Medicine, 1990, p. 54.

Schmiedl, U. P., et al, Society of Magnetic Resonance in Medicine, 1990, p. 643

White, D. L., et al, Society of Magnetic Resonance in Medicine, 1989, p. 807.

Weinmann, H. J., et al, Physiological Chemistry and Physics and Medical NMR, 16, 167–172 (1980).

Database WPI/Derwent, abstract of JP 7002679 (Jan. 6, 1995) and Application No. 930139356.

Washburn, L. C., et al., Nucl. Med. Biol., vol. 18, No. 3, 313–322 (1991).

Blix, G., Acta Chemica Scandinavica, vol. 2, 467–473 (1948).

*Primary Examiner*—John Kight
*Assistant Examiner*—Dameron Jones

[57] ABSTRACT

There is disclosed a diagnostic imaging agent which comprises a compound wherein at least one bifunctional ligand is chemically bonded to an amino group of amino oligosaccharide having the molecular weight of 500 to 2000 and having a reduction-treated reducing end of a sugar chain, or to an aldehyde group of a dialdehyde-oligosaccharide, at least one constituent monosaccharide of which is oxidation-cleaved, having the molecular weight of 500 to 2000 and having a reduction-treated reducing end of a sugar chain, and said ligand is coordinated with at least one metal ion selected from the group consisting of metal ions having the atomic number of 21–29, 31, 32, 37–39, 42–44, 49 and 56–83.

8 Claims, 1 Drawing Sheet

DIAGNOSTIC IMAGING AGENT WITH BACKBONE WITH MODIFIED SUGAR CHAIN END

FIELD OF THE INVENTION

The present invention relates to a diagnostic imaging agent, more particularly, to a diagnostic imaging agent useful for nuclear magnetic resonance, X-ray and radiation image diagnosis, which contains a metal complex compound of an oligosaccharide skeleton having a reduction-treated reducing end.

BACKGROUND OF THE INVENTION

Diethylenetriaminepentaacetic acid gadolinate (hereinafter abbreviated as "DTPA-Gd")[JP-A 58-29718] which is widely used as a nuclear magnetic resonance diagnostic agent is a typical example of monometal complexes and the effectiveness thereof as a diagnostic imaging agent in the brain or the spinal cord region has almost been established. However, the relaxivity of DTPA-Gd is lower than that of Gd itself, because Gd is chelated with DTPA. Therefore, there is a need for compensating for the lowered relaxivity with the increased dosage or the like. In addition, DTPA-Gd is rapidly excreted into the urine after administration [Hiroki Yoshikawa et al., Gazoshindan, 6, 959–969, 1986], and this is very disadvantageous for imaging of several parts of the body by reflecting them in blood stream (blood vessel distribution, blood stream distribution, distribution volume, permeation and the like in a lesion) with a single injection of the pharmaceutical. Further, such the rapid excretion also makes distribution properties of DTPA-Gd extremely disadvantageous.

In order to solve these problems, a diagnostic imaging agent obtained by chemically bonding a bifunctional ligand to an amino oligosaccharide and coordinating a metal ion thereto via this bifunctional ligand [JP-A 5-97712], and a diagnostic imaging agent obtained by chemically bonding at least one bifunctional ligand to a dialdehyde-saccharide wherein a plurality of D-glucose molecules are bonded and at least one constituent monosaccharide among them is oxidation-cleaved [JP-A 5-25059] are developed. However, it was found that, when a raw material saccharide, an important component of these compounds, is left or reacted for a longer period of time, the intramolecular or intermolecular bonding of the saccharide, or peroxidation of the saccharide by an oxidizing agent occurs in an aqueous solution unless a reducing end of a sugar chain has been treated.

OBJECTS OF THE INVENTION

The main object of the present invention is to provide a diagnostic imaging agent useful for nuclear magnetic resonance, X-ray and radiation image diagnosis, which can be easily prepared using an oligosaccharide skeleton without inducing unnecessary side reactions, has the stability and the good solubility in water and is physiologically acceptable.

This object as well as other objects and advantages of the present invention will become apparent to those skilled in the art from the following description with reference to the accompanying drawing.

SUMMARY OF THE INVENTION

The present inventors studied hard and, as the result, we found that, by reduction-treating a reducing end of a sugar chain of a starting raw material oligosaccharide, the above-described side reactions can be avoided and the resulting metal complex compound is a diagnostic imaging agent useful for nuclear magnetic resonance, X-ray and radiation image diagnosis, which has the stability and the good solubility in water and is physiologically acceptable.

That is, the present invention provides a diagnostic imaging agent which comprises a compound wherein at least one bifunctional ligand is chemically bonded to an amino group of amino oligosaccharide having the molecular weight of 500 to 2000 and having a reduction-treated reducing end of a sugar chain, or to an aldehyde group of a dialdehyde-oligosaccharide, at least one constituent monosaccharide of which is oxidation-cleaved, having the molecular weight of 500 to 2000 and having a reduction-treated reducing end of a sugar chain, and said ligand is coordinated with at least one metal ion selected from the group consisting of metal ions having the atomic number of 21–29, 31, 32, 37–39, 42–44, 49 and 56–83.

DETAILED DESCRIPTION OF THE INVENTION

Figure 1:
FIG. 1 is a nuclear magnetic resonance image showing a transverse view of the cancer carrying part of a rat after administration of R-CHI5-DTPA-Gd solution.

The reduction-treating of a reducing end of a sugar chain of an oligosaccharide is carried out by the known method such as a method using sodium borohydride, a catalytic reduction method using hydrogen or the like. For example, a chitosan trimer is dissolved in water, and sodium borohydride is added thereto, followed by stirring at room temperature under reduced pressure and the addition of hydrochloric acid to adjust the solution to acidic. The disappearance of a reducing end can be confirmed according to a Blix method [Blix, G.: Acta Chem. Scand., 2, 467, 1948]. Alternatively, a commercially available pre-reduction-treated maltotetraitol and the like may be used. Examples of an oligosaccharide are amino oligosaccharide, and dialdehyde-saccharide such as maltotriose, maltotetraose, maltopentaose, maltohexaose, maltoheptaose, isomaltotriose, isomaltotetraose, isomaltopentaose, isomaltohexaose, isomaltoheptaose, cellotriose, cellotetraose, cellopentaose, cellohexaose, laminaritriose, laminaritetraose, laminaripentaose, laminarihexaose, laminariheptaose, ellulose, panose, raffinose and the like.

Preferable examples of amino oligosaccharide is tri- to deca- saccharides such as chitosan oligosaccharide and galactosamino oligosaccharide. Particularly preferable examples of amino oligosaccharide are tri- to hexa- saccharides such as chitosan oligosaccharide and galactosamino oligosaccharide.

As a bifunctional ligand, a linear or cyclic polyaminopolycarboxylic acid having a crosslinking chain part which can be coupled to a 2-positional amino group when a saccharide to be reduction-treated is amino oligosaccharide, and to an aldehyde group when a saccharide to be reduction-treated is dialdehyde oligosaccharide is used. Preferable coordinating structure is a bifunctional ligand such as diethylenetriaminepentaacetic acid (hereinafter abbreviated as "DTPA"), 1,4,7,10-tetraazacyclododecane-1,4,7,10-tetraacetic acid (hereinafter abbreviated as "DOTA"), or 1,4,8,11-tetraazacyclotetradecane-1,4,8,11-tetraacetic acid, and derivatives thereof. Examples of a preferable reactive group of a crosslinking chain part of a bifunctional ligand which can be coupled to a 2-positional amino group are activated halogen, alkoxyester, succinimidiester, isothiocyanate, anhydride and the like. More particularly, there are 1-(p-isothiocyanatobenzyl)-DTPA [Martin, W. B. et al.: Inorg. Chem., 25, 2772–2781, 1986], DTPA dianhydride, 2-(p-isothiocyanatobenzyl)-DOTA [U.S. Pat. No. 4,678,667] and the like. A suitable bifunctional ligand which can be coupled to an aldehyde group has an activated amino group. More particularly, there are 1-(p-aminobenzyl)-DTPA [Martin, W. B. et al.: Inorg. Chem., 25, 2772–2781, 1986], 2-(p-aminobenzyl)-DOTA [U.S. Pat. No. 4,678,667], 2-aminobutyl-DOTA [Parker, D. et al.: Pure & Appl. Chem. 61, 1637–1641, 1989], 1,4,7,10-tetraazacyclododecane-1-aminoethylcarbamoylmethyl-4,7,10-tris[(R,S)-methylacetic acid] and the like.

The coupling of a reduction-treated oligosaccharide with a bifunctional ligand is carried out according to the known method. For example, both a dialdehyde-saccharide obtained by oxidation-cleaving the reduction-treated oligosaccharide and a bifunctional ligand having an activated amino group as a reactive group are reacted at room temperature in an alkaline solution to obtain a desired compound. In this case, since in situ reaction can be proceeded without consideration of side reactions by an oxidizing agent used for preparation of the dialdehyde-saccharide from a reduction-treated oligosaccharide, a reaction becomes easy. Furthermore, the complicated purification procedures during synthesis becomes unnecessary, which resulted in simpler synthesis procedures. If necessary, this coupled compound may be reduced to convert —CH=N— into —CH$_2$—NH—. Alternatively, a bifunctional ligand may be pre-chelated with a metal.

In the present invention, a metal ion is selected from metal ions having the atomic number of 21–29, 31, 32, 37–39, 42–44, 49 and 56–83 depending upon the use of image diagnosis. When the diagnostic imaging agent of the present invention is used for nuclear magnetic resonance image diagnosis, a metal ion should be paramagnetic and is selected from an ion of an element having the atomic number of 26 and lanthanide ions having the atomic number of 57–70. Preferable metal ions are Gd, Dy, Tb, Ho, Er and Fe ion. When the diagnostic imaging agent of the present invention is used for X-ray diagnosis, a metal ion is selected from the group consisting of lanthanide ions having the atomic number of 57–70 and element ions having the atomic number of 56, 76, 82 and 83. Suitable metal ions are Bi, Pb and Os ion. When the diagnostic imaging agent of the present invention is used as a radiation diagnostic imaging agent, a metal ion must be radioactive. Suitable metal ions are radioactive Co, Cu, Ga, Ge, Sr, Y, Tc, In, Sm, Yb, Re and Ir ion. A metal ion to be used may be a metal itself or an inorganic compound thereof (for example, chloride, oxide and the like). Chelation is carried out according to the conventional method.

In the resulting metal complex compound, at least one bifunctional ligand is chemically bonded to a reduction-treated oligosaccharide and a metal ion is coordinated thereto.

The dose of a diagnostic imaging agent of the present invention is selected depending upon the use of image diagnosis. For example, when used as a nuclear magnetic resonance imaging agent, the dose of the metal ion is generally 0.001 to 10 mmol/kg, preferably 0.05 to 0.5 mmol/kg. When used as a X-ray diagnostic imaging agent, the dose of the metal ion is 0.01 to 20 mmol/kg, preferably 0.1 to 10 mmol/kg. When used as a radiation diagnostic agent, an radioactive amount of 370 to 18500 MBq is administered. Usually, the diagnostic imaging agent of the present invention is administered intravenously and, in some cases, can be administered orally or intra-arterially.

The diagnostic imaging agent of the present invention has retention in the blood of in a range of blood half-life of 0.5 to 5 hours which is considered to be clinically effective. This is effective for improving the collection efficacy of proton relaxation effects by an imaging agent. In addition, the higher relaxation effect per unit weight of a metal has the advantages. For example, in the case of diagnosis with a lower magnetic field nuclear magnetic resonance apparatus having the lower collection efficacy of proton relaxation effect, since the diagnostic imaging agent of the present invention has the higher relaxation effect per unit weight of a metal, the detection efficacy is improved and time necessary for imaging can be shortened. Furthermore, since the diagnostic imaging agent of the present invention has the larger shortening effect in relaxation time per one molecule than that of DTPA-Gd, it can be used at a lower dose than that of DTPA-Gd when the same imaging effect as that of DTPA-Gd is desired in the same magnetic field intensity apparatus, which results in the advantages in the safety. On the contrary, the diagnostic imaging agent of the present invention can afford more information on the living body at the same dose and, therefore, the clinical usefulness is improved. Therefore, the present invention can provide an imaging agent having the suitable retention in the blood and effective imaging effect for the magnetic field intensity of a nuclear magnetic resonance apparatus and imaging conditions.

In addition, since the diagnostic imaging agent of the present invention shows the suitable retention in the blood, the evaluation of blood vessel distribution (vascularity) can be performed. Therefore, since the diagnostic imaging agent of the present invention can image the blood vessel without using particular pulse sequence for MR angiography which has been remarkably advanced recently, it is also useful as a diagnostic imaging agent for intravenous administration.

Since the diagnostic imaging agent of the present invention has the good solubility in water, the compound itself can be prepared into a solution containing the compound in the high concentration. Accordingly, a solubilizer is not necessarily required upon preparation of the solution. In addition, since the diagnostic imaging agent of the present invention is a polychelate compound, it can decrease the total molality in the preparation of a solution in comparison with a monometal complex, which results in decrease in osmotic pressure. These alleviate the load to volume of the circulatory system or body fluid equilibrium upon administration in the living body, which results in advantage in the safety.

The diagnostic imaging agent of the present invention can be formulated into preparations by dissolving in distilled water for injection or physiologically compatible aqueous solvent. If necessary, a pH adjusting agent or a solubilizer may be added thereto. Examples of a pH adjusting agent are sodium hydroxide and hydrochloric acid and an example of a solubilizer is N-methylglucamine.

Following Examples further illustrate the present invention in detail but are not to be construed to limit the scope thereof. The abbreviations used in Examples are as follows:

DTPA: diethylenetriaminepentaacetic acid

DO3MA : 1,4,7,10-tetraazacyclododecane-1-aminoethylcarbamoylmethyl-4,7,10-tris[(R,S)-methylacetic acid]

R-CHI3: chitosan trimer in which a reducing end is reduction-treated

R-CHI5: chitosan pentamer in which a reducing end is reduction-treated

R-GLU4: maltotetraitol

EXAMPLE 1

Synthesis of R-CHI3-DTPA-Gd

Chitosan trimer (10 g; 16.3 mmol) was dissolved in distilled water (300 ml) and a lM aqueous solution of sodium hydroxide was added to adjust pH to 8. Sodium borohydride (1.9 g; 51.3 mmol) was added thereto, followed by stirring for 3.5 hours under reduced pressure. 2M hydrochloric acid was added to adjust pH to about 2, followed by electrodialysis to desalt, to obtain a product (9 g). An amino group was confirmed by a ninhydrin method, a saccharide skeleton was confirmed by a sulfuric acid coloring method and the treatment of a reducing end was confirmed by a Blix method. As the result, it was confirmed that the product is R-CHI3.

R-CHI3 (1.0 g; 1.63 mmol) was dissolved in distilled water (10 ml), a 10M aqueous solution of sodium hydroxide (5 ml) and subsequently DTPA dianhydride (7.16 g; 20.0 mmol) were rapidly added, followed by stirring for 3 hours. Then, gadolinium chloride hexahydrate (7.45 g; 20.0 mmol) was added and a suitable amount of a 1M aqueous solution of sodium hydroxide was added to adjust pH to 7, followed by stirring for 30 minutes. Electrodialysis was carried out for 120 hours to remove excess DTPA dianhydride, followed by concentrated to dryness, to obtain white crystals (450 mg). The content of Gd was 15.8 wt %.

EXAMPLE 2

Synthesis of R-CHI5-DTPA-Gd

According to the same manner as that of Example 1 for synthesis of R-CHI3, R-CHI5-DTPA-Gd was synthesized. R-CHI5 (100 g; 99.4 mmol) was dissolved in distilled water (1500 ml), a 10M aqueous solution of sodium hydroxide (600 ml) and subsequently anhydrous DTPA (700 g; 1981 mmol) were added rapidly, followed by stirring for 3 hours. Then, gadolinium chloride hexahydrate (884 g; 2377 mmol) was added to adjust pH to 7, followed by stirring for 30 minutes. Electrodialysis was carried out for 400 hours to remove excess DTPA-Gd, followed by concentration to dryness, to obtain white crystals (200 g). The content of Gd was 19.5 wt %.

EXAMPLE 3

Synthesis of R-GLU4-DO3MA-Bi

DO3MA (3.0 g; 5.7 mmol) was dissolved in distilled water (150 ml), bismuth chloride (1.8 g; 5.7 mmol) was added thereto, and a 1M aqueous solution of sodium hydroxide was added to adjust pH to 7. Thereafter, the solution was heated while stirring at 60° C. for 24 hours, filtered and concentrated to dryness, to obtain a compound DO3MA-Bi (5.1 g) wherein bismuth is chelated to DO3MA.

Commercially available maltotetraitol (0.5 g; 0.75 mmol) wherein a reducing end had been reduction-treated was dissolved in distilled water (15 ml) and a 0.2M aqueous solution of sodium metaperiodate (25 ml) was added in portions, followed by stirring for 1 hour. Then, DO3MA-Bi (1.8 g; 2.4 mmol) and triethylamine (0.25 g; 2.4 mmol) were added, followed by stirring at room temperature for 24 hours. Sodium borohydride (0.1 g; 2.4 mmol) was added thereto to stir for 4 hours, followed by filtration to remove precipitates. Then, 1M hydrochloric acid was added in portions to lower pH to 5 to remove excess sodium borohydride, the precipitates were removed by filtration and a 1M aqueous solution of sodium hydroxide was added to adjust pH to 7. Purification was carried out for 40 hours by dialysis (dialysis membrane of fractionation molecular weight; 500), followed by concentration to dryness, to obtain white crystals (170 mg). The content of Bi was 14.1 wt %.

EXAMPLE 4

Measurement of relaxivity of R-CHI3-DTPA-Gd (in vitro experiment)

The relaxivity of R-CHI3-DTPA-Gd and that of DTPA-Gd as a control were measured. R-CHI3-DTPA-Gd or DTPA-Gd was dissolved in water to obtain an aqueous solution having the Gd concentration of 4, 2, 1 and 0.5 mM. The relation with water proton exposed to the compounds was determined as relaxation time at 37° C. (T1 and T2; msec) using NMR (0.5T and 1.5T) and the relaxivity (R1 and R2; $(mM \cdot S)^{-1}$) was calculated based on relaxation time values. The results are shown in Table 1.

R-CHI3-DTPA-Gd was found to have the good in vitro relaxation effect, which is apparently higher than that of a monometal complex, DTPA-Gd, determined according to the similar procedures. As the results, the effectiveness of R-CHI3-DTPA-Gd was confirmed.

TABLE 1

| Relaxivity of R—CHI3-DTPA—Gd and DTPA—Gd | | | |
|---|---|---|---|
| Compound | Magnetic field intensity | R1 $(mM \cdot S)^{-1}$ | R2 $(mM \cdot S)^{-1}$ |
| R—CHI3-DTPA—Gd | 0.5T | 9.17 | 11.13 |
|  | 1.5T | 8.86 | 10.87 |
| DTPA—Gd | 0.5T | 3.7 | 4.5 |

EXAMPLE 5

Measurement of relaxivity of R-CHI5-DTPA-Gd (in vitro experiment)

The relaxivity of R-CHI5-DTPA-Gd and that of DTPA-Gd as a control were measured. R-CHI5-DTPA-Gd or DTPA-Gd was dissolved in water to obtain an aqueous solution having the Gd concentration of 4, 2, 1 and 0.5 mM. The relation with water proton exposed to the compounds was determined as relaxation time (T1 and T2; msec) at 37° C. using NMR (0.5T) and the relaxivity (R1 and R2; $(mM \cdot S)^{-1}$) was calculated based on relaxation time values. The results are shown in Table 2. R-CHI5-DTPA-Gd was found to have the good in vitro relaxivity effect which is apparently higher than that of a monometal complex, DTPA-Gd, determined according to the similar manner and the effectiveness of R-CHI5-DTPA-Gd was confirmed.

TABLE 2

Relaxivity of R—CHI5-DTPA—Gd and DTPA—Gd

| Compound | Magnetic field intensity | R1 (mM · S)$^{-1}$ | R2 (mM · S)$^{-1}$ |
|---|---|---|---|
| R—CHI5-DTPA—Gd | 0.5T | 10.5 | 12.7 |
| DTPA—Gd | 0.5T | 3.7 | 4.5 |

EXAMPLE 6

Examination of stability of R-CHI3

Regarding an amino group of a functional group of R-CHI3, when a crosslinking chain part of a bifunctional ligand is, for example, acid halide, a basic catalyst must be added upon its reaction. The stability of R-CHI3 and chitosan trimer (CHI3) in which a reducing end had not been treated was examined in the presence of potassium carbonate as a basic catalyst. Each 1 g of R-CHI3 and CHI3 was dissolved in a 0.5M aqueous solution of potassium carbonate. The solution was stirred at room temperature and the stability of the compounds was determined using a thin layer chromatography method (stationary phase; silica gel 60, mobile phase; chloroform:methanol:aqueous ammonia= 2:2:1, detection; ninhydrin method). Immediately after stirring, R-CHI3 was developed at the position of Rf=0.08 and CHI3 was developed at the position of Rf=0.17. At 12 hours after stirring, R-CHI3 was developed at the position of Rf=0.08 as observed immediately after stirring, while a spot of Rf=0.17 disappeared and coloring was newly observed at the origin part in the case of CHI3. From these results, it was confirmed that R-CHI3 is stable in the presence of a basic catalyst in a reaction requiring a longer period of time.

EXAMPLE 7

Imaging effect of R-CHI5-DTPA-Gd in a rat carrying cancer

A solution of R-CHI5-DTPA-Gd (0.5M Gd) was administered to a female WKA rat (200 g, transplanted with rat hepatocyte cancer kDH-8) anesthetized with ravonal via a cannula fixed to tail vein (0.2 mmol Gd/kg), the rat was fixed prone in a nuclear magnetic resonance imaging apparatus (Omega CSI manufactured by Bruker), and the cancer carrying part was imaged using an imaging coil for rat body at magnetic field intensity of 2T.

Imaging was carried out according to spin echo method of T1 weighted (TR=600 msec, TE=12 msec) under the condition of 2 mm in slice thickness, a resolution of 256×128. The results thereof are shown in FIG. 1. From these results, it was confirmed that the cancer carrying part of female WKA rat is well imaged by R-CHI5-DTPA-Gd.

What is claimed is:

1. A diagnostic imaging agent which comprises a compound wherein at least one bifunctional ligand is chemically bonded to an amino group of amino oligosaccharide composed of three to six monosaccharides and having a reduction-treated reducing end of a sugar chain, or to an aldehyde group of a dialdehyde-oligosaccharide composed of three to six monosaccharides, at least one constituent monosaccharide of which is oxidation-cleaved, and having a reduction-treated reducing end of a sugar chain, and said ligand is coordinated with at least one metal ion selected from the group consisting of metal ions having the atomic number of 21–29, 31, 32, 37–39, 42–44, 49 and 56–83.

2. A diagnostic imaging agent according to claim 1, wherein amino oligosaccharide to be reduction-treated is chitosan oligosaccharide or galactosamino oligosaccharide.

3. A diagnostic imaging agent according to claim 1, wherein dialdehyde-oligosaccharide is oxidation-cleaved malto oligosaccharide, isomalto oligosaccharide, laminari oligosaccharide or gentio oligosaccharide having D-glucose as a constituent monosaccharide.

4. A diagnostic imaging agent according to claim 1, wherein the bifunctional ligand is linear or cyclic polyaminopolycarboxylic acid.

5. A diagnostic imaging agent according to claim 4, polyaminopolycarboxylic acid is diethylenetriaminepentaacetic acid, 1,4,7,10-tetraazacyclododecane-1,4,7,10-tetraacetic acid or 1,4,8,11-tetraazacyclotetradecane-1,4,8, 11-tetraacetic acid or derivatives thereof.

6. A diagnostic imaging agent according to any one of claims 1, 2 or 3, wherein the metal ion is Gd, Dy, Tb, Ho, Er or Fe ion.

7. A diagnostic imaging agent according to any one of claims 1, 2 or 3, wherein the metal ion is Bi, Pb or Os ion.

8. A diagnostic imaging agent according to any one of claims 1, 2 or 3, wherein the metal ion is radioactive Co, Cu, Ga, Ge, Sr, Y, Tc, In, Sm, Yb, Re or Ir ion.

* * * * *